United States Patent [19]

Mase et al.

[11] Patent Number: 4,610,741
[45] Date of Patent: Sep. 9, 1986

[54] PROCESS OF MANUFACTURING ELECTROCHEMICAL DEVICE

[75] Inventors: Syunzo Mase, Aichi; Shigeo Soejima, Nagoya, both of Japan

[73] Assignee: NGK Insulators, Ltd., Japan

[21] Appl. No.: 683,139

[22] Filed: Dec. 18, 1984

[30] Foreign Application Priority Data

Dec. 24, 1983 [JP] Japan .................. 58-251675

[51] Int. Cl.$^4$ ............ C03B 29/00; C04B 33/34
[52] U.S. Cl. .................. 156/89; 204/412; 204/424; 204/426; 29/592 R
[58] Field of Search ........... 204/421, 424, 425, 426, 204/427, 428, 429, 412; 29/592 R; 156/89

[56] References Cited

U.S. PATENT DOCUMENTS

| | | | |
|---|---|---|---|
| 4,282,080 | 8/1981 | Muller et al. | 204/428 X |
| 4,294,679 | 10/1981 | Maurer et al. | 29/592 R X |
| 4,334,974 | 6/1982 | Muller et al. | 204/425 |
| 4,441,981 | 4/1984 | Okamoto et al. | 204/426 |
| 4,450,065 | 5/1984 | Yamada et al. | 204/425 X |
| 4,498,968 | 2/1985 | Yamada et al. | 204/425 X |
| 4,505,806 | 3/1985 | Yamada | 204/425 |
| 4,505,807 | 3/1985 | Yamada | 204/425 |

FOREIGN PATENT DOCUMENTS

| | | |
|---|---|---|
| 0020938 | 1/1981 | European Pat. Off. . |
| 0035400 | 3/1981 | European Pat. Off. . |
| 0052542 | 10/1981 | European Pat. Off. . |
| 2449887 | 9/1980 | France . |
| 3215998 | 11/1982 | Fed. Rep. of Germany . |
| 58-32156 | 2/1983 | Japan . |
| 2050625 | 1/1981 | United Kingdom . |
| 2054868 | 2/1981 | United Kingdom . |

OTHER PUBLICATIONS

European Search Report 843089918.6; EP 84 30 8918 (pp. 1-3).

Primary Examiner—John F. Niebling
Assistant Examiner—Nam X. Nguyen
Attorney, Agent, or Firm—Parkhurst & Oliff

[57] ABSTRACT

A process of manufacturing an electrochemical device including a pumping cell having a first and a second electrode, and a sensing cell having a third and fourth electrode such that the electrodes are disposed on at least one solid electrolyte body, and the second and fourth electrodes are exposed to the atmosphere in an internal cavity formed in the device. The process comprises a step of interposing an insert consisting essentially of a sublimable material in the cavity to be formed during superposition of green sheets or layers of the solid electrolyte bodies and electrodes into an unfired laminar structure, such that the insert is disposed opposite to the unfired layers of the second and fourth electrodes, and further comprises a step of co-firing the unfired laminar structure incorporating the insert so as to cause the insert to disappear through sublimation. The insert prevents portions of the solid electrolyte bodies from being extruded or displaced into the cavity while the stack of the green sheets of solid electrolyte is compressed into the unfired laminar structure.

23 Claims, 12 Drawing Figures

PROCESS OF MANUFACTURING ELECTROCHEMICAL DEVICE

BACKGROUND OF THE INVENTION

The present invention relates generally to a process of manufacturing an electrochemical device, and more particularly to an improved process of manufacturing an electrochemical device of laminar structure comprising solid electrolyte layers.

There have been known various electrochemical devices (electrochemical sensing elements) using solid electrolyte, for example, oxygen sensors to detect the oxygen concentration of an exhaust gas emitted from internal combustion engines of automotive vehicles. Typical examples of such oxygen sensors include an oxygen sensor which comprises a body of oxygen-ion conductive solid electrolyte such as zirconia ceramics and which operates to determine the oxygen concentration according to the principle of an oxygen concentration cell. Also known in the prior art are electrochemical devices such as sensing and pumping elements or cells for hydrogen, nitrogen, carbon dioxide, etc. In such electrochemical cells, solid electrolyte materials have been generally used in the form of a tubular body which has an elongate bore closed at its one end. In recent years, however, it has been attempted to replace the tubular solid electrolyte body with a solid electrolyte body of planar shape as disclosed in U.S. Pat. Nos. 4,334,974; 4,282,080; and 4,300,990, in view of relatively low productivity and high cost of manufacture of solid electrolyte bodies of tubular type, and for the benefit of easy assembling of parts with a planar solid electrolyte body to form an electrochemical device. When such planar solid electrolyte bodies (i.e., solid electrolyte in the form of layers or sheets) are employed, suitable electrodes are disposed on the surfaces of the layer or layers of solid electrolyte, and the electrolyte layers and other layers or parts are assembled as a stack into a laminar structure constituting an electrochemical device or sensing element.

One exemplary form of a known electrochemical device of laminar structure comprises an electrochemical pumping cell having a first and a second electrode disposed on a planar solid electrolyte body, and an electrochemical sensing cell having a third and a fourth electrode disposed on another planar solid electrolyte body. These pumping and sensing cells are constructed such that the second and fourth electrodes (inner pumping and measuring electrodes) are exposed to the atmosphere in an internal cavity that is defined by the above solid electrolyte bodies and usually also by a spacer member which is sandwiched by the solid electrolyte bodies and which may also be a solid electrolyte body. For easy manufacture of such an electrochemcial device, it is proposed to employ a process which comprises the steps of: superposing unfired planar solid electrolyte bodies (green sheets or unfired layers of solid electrolyte) in a stack such that a cavity of a suitable volume is formed within the stack; forming unfired layers of electrodes on the green sheets of solid electrolyte as required; applying a pressure to compress the laminated stack of the solid electrolyte and electrodes to form an unfired integral laminar structure; and co-firing the laminar structure at a suitable sintering temperature of the solid electrolyte.

In the above introduced manufacturing process wherein the unfired green sheets of solid electrolyte are laminated under pressure into an integral laminar structure, the internal cavity formed by the green sheets during the laminating step is more or less deformed due to the compressing pressure applied to the green sheets. As a result, the cavity formed in the fired laminar structure of one electrochemical device tends to have different volume and shape from those of the cavity formed in the other devices. Different volumes and shapes of the cavities lead to inconsistent operating characteristics and performance between the electrochemical devices, thereby causing these devices to fail to satisfy the practical requirements. Although the aforementioned deformation (reduction in volume) of the internal cavity may be avoided by reducing the pressure to be applied to the stacked assembly, the reduced pressure causes difficulty in attaining sufficient mutual adhesion or bonding of the individual green sheets of solid electrolyte, and consequently leads to a decline in the yield of the products. Hence, the adoption of such solution to the above problem is far beyond possibility.

SUMMARY OF THE INVENTION

The present invention was developed in the light of the foregoing technological background in the art. It is therefore an object of the invention to provide a process suitable for manufacturing an electrochemical device which has an internal cavity with a constant volume as intended, and assures improved consistency in operating characteristics between the devices.

According to the present invention, there is provided a process of manufacturing an electrochemical device including an electrochemical pumping cell having a first and a second electrode, and an electrochemical sensing cell having a third and a fourth electrode such that the electrodes are disposed on at least one of plural generally planar solid electrolyte bodies and the second and fourth electrodes are exposed to an internal cavity formed in an assembly of the pumping and sensing cells, the process comprising the steps of superposing unfired layers of the solid electrolyte bodies on each other to form an unfired integral laminar structure with unfired layers of the electrodes disposed on at least one of the unfired layers of the solid electrolyte bodies such that the internal cavity is formed with a predetermined volume in said laminar structure and such that the unfired layers of the second and fourth electrodes are exposed to the internal cavity, characterized in that an insert of a predetermined volume is interposed in the internal cavity to be formed during the superposition of said unfired layers of the solid electrolyte bodies and electrodes into said unfired integral laminar structure such that said insert is disposed opposite to exposed surfaces of said unfired layers of the second and fourth electrodes, said insert comprising as a major component thereof a sublimable material which sublimes at an elevated temperature, and said unfired integral laminar structure is co-fired at a predetermined sintering temperature and causing the insert to disappear by means of sublimation.

In the process of the invention as described above, the unfired layers or green sheets of the solid electrolyte bodies are superposed on each other into an unfired integral laminar structure while an insert of a predetermined volume which can sublime by heat and thus disappears at the sintering temperature is disposed in the internal cavity of a suitable volume which is formed in the laminar structure. The insert interposed in the internal cavity in the unfired laminar structure effectively protects the internal cavity against otherwise possible deformation or displacement of portions of the unfired geeen sheets or layers of the solid electrolyte bodies (and therefore of the unfired layers of the electrodes) toward the space in the otherwise existing cavity when the superposed green sheets are compressed during preparation of the unfired integral laminer structure. In the subsequent process of sintering or firing the green sheets of solid electrolyte the insert in the internal cavity will sublime and disappear, that is, it does not remain in the cavity in the fired assembly of the electrochemical device. Thus, the use of the insert has no adverse effect on the product. Rather, the insert facilitates the formation of an internal cavity without deformation thereof or variation in its volume, and consequently contributes to easy fabrication of an electrochemical device having improved sensing characteristics.

According to one embodiment of the invention, the internal cavity is substantially filled with the sublimable insert.

According to another embodiment of the invention, the sublimable material is selected so that it sublimes at a temperature higher than a decomposition point of thermally decomposable substances contained in the unfired layers of the solid electrolyte bodies. Preferably, theobromine or indigo is used as the sublimable material for the insert.

In the case where the second and fourth electrodes are disposed on the same surface of the same solid electrolyte body, the cavity may be an elongate rectangular flat space to which the second and fourth electrodes are exposed in spaced-apart relation with each other along the surface of the solid electrolyte body.

When the second and fourth electrodes are disposed on different solid electrolyte bodies, the insert is sandwiched between the unfired layers of the second and fourth electrodes.

According to a further embodiment of the invention, the process may further comprise a step of forming diffusion-resistance means for communication between an outside measurement atmosphere and the internal cavity, the diffusion-resistance means having a predetermined diffusion resistance to molecules of a component of the outside measurement atmosphere.

In one advantageous form of the above embodiment of the invention, the diffusion-resistance means is formed by forming an aperture through the thicknesses of the unfired layers of the first and second electrodes and the solid electrolyte of the electrochemical pumping cell, the aperture having a small diameter which is selected so as to provide the predetermined diffusion resistance.

In alternative form of the above embodiment, the diffusion-resistance means is formed by opposing two electrochemical cells toward each other, which are pumping cell and sensing cell, with a small distance therebetween, which is selected so as to provide said predetermined diffusion resistance.

In accordance with another aspect of the invention, there is provided a process of manufacturing an electrochemical device including an electrochemical pumping cell having a first and a second electrode, and an electrochemical sensing cell having a third and a fourth electrode, such that the electrodes are disposed on at least one of a plurality of planar solid electrolyte bodies and such that the third electrode is exposed to a reference gas existing in a reference-gas passage formed in an assembly of the electrochemical pumping and sensing cells, the process comprising the steps of superposing unfired layers of the solid electrolyte bodies on each other to form an unfired integral laminar structure with unfired layers of the electrodes disposed on at least one of the unfired layers of the solid electrolyte bodies such that the reference-gas passage is formed with a predetermined volume in the unfired integral laminar structure and such that the unfired layer of the third electrode is exposed to the reference-gas passage, characterized in that the process further comprises the steps of:

interposing an insert of a predetermined volume in the reference-gas passage to be formed during the superposition of the unfired layers of the solid electrolyte bodies and electrodes into the unfired integral laminar structure such that the insert is disposed opposite to an exposed surface of the unfired layer of the third electrode, the insert comprising as a major component thereof a sublimable material which sublimes at an elevated temperature; and co-firing the unfired integral laminar structure at a predetermined sintering temperature and causing said insert to disappear by means of sublimation.

It will be obvious that the above process according to another aspect of the invention may be practiced to produce an electrochemical device which does not include an electrochemical pumping cell having a first and a second electrode. In this case, the electrochemical device includes only an electrochemical sensing cell which has a third electrode exposed to a reference gas in the reference-gas passage, and a fourth electrode exposed to an outside measurement gas.

BRIEF DESCRIPTION OF THE DRAWING

The above and other objects, features and advantages of the present invention will become more apparent from reading the following description taken in connection with the accompanying drawing in which.

DETAILED DESCRIPTION OF THE INVENTION

To further clarify the subject matter of the present invention, the invention will be described in detail referring to the accompanying drawings.

Figure 1:
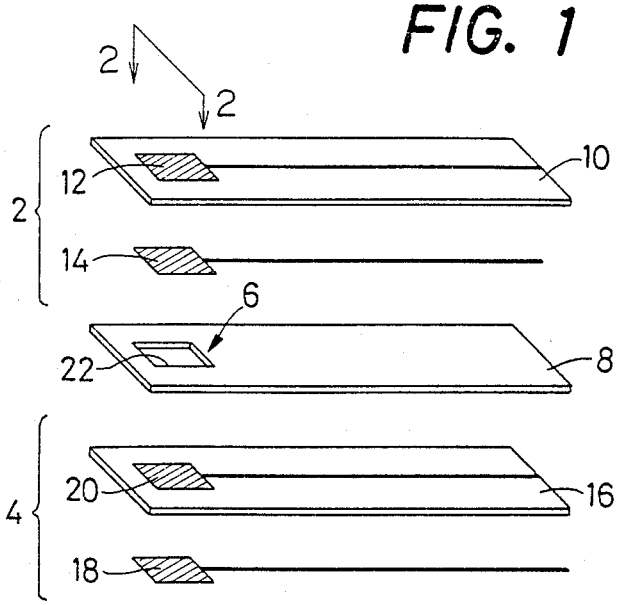
FIG. 1 is an exploded perspective view of one example of an electrochemical device in the form of an oxygen sensor, which is suitably produced according to the process of the present invention.

An exploded perspective view of FIG. 1 shows a sensing element of one example of an electrochemcial device or sensing element in the form of an oxygen concentration detector, i.e., an oxygen sensor which the present invention may be carried into effect. This oxygen sensor is a so-called "lean-burn" sensor which is an integral co-fired lamination comprising an oxygen pumping cell 2, an oxygen concentration sensing cell 4, and a planar spacer member 8 which is made of a ceramic material and has a rectangular cutout 22 for defining an internal cavity 6. The pumping and sensing cells 2, 4 and the spacer member 8 are superposed on each other in a stack to form a laminar assembly with the spacer member 8 sandwiched between the pumping and sensing cells 2, 4.

The oxygen pumping cell 2 has a planar solid electrolyte body 10 made of zirconia ceramics or the like, and an outer pumping electrode (first electrode) 12 made of a porous layer of platinum, for example, which is disposed on one of opposite surfaces of the planar solid electrolyte body 10, that is, on the outer surface thereof which is exposed to an exhaust gas or other gases to be measured (hereinafter referred to "measurement gas or atmosphere"). The outer pumping electrode 12 is connected to an external power source through its lead connected thereto. On the other (inner) surface of the planar solid electrolyte body 10, there is disposed an inner pumping electrode (second electrode) 14 which is made of the same material as the outer pumping electrode 12, i.e., made of a porous layer of platinum. The inner pumping electrode 14 is also connected to the external power source through its lead connected thereto.

As indicated above, the oxygen pumping cell 2 is an electrochemical cell which is constituted by the planar solid electrolyte body 10 and the pair of electrodes 12, 14 which are disposed in contact with the outer and inner surfaces of the solid electrolyte body 10. With a DC voltage applied between these two electrodes 12, 14, the oxygen pumping cell 2 operates in the well known manner, to introduce the oxygen in the outside measurement gas into the internal cavity 6 defined in the spacer member 8, and to discharge or remove the oxygen from the cavity 6 out into the outside measurement gas through the planar solid electrolyte body 10. The amounts of the oxygen to be introduced and discharged are varied in proportion to the amount of current flowing through the pumping cell 2.

In the meantime, the oxygen concentration cell 4 which consists of the same construction as the pumping cell 2, includes a planar solid electrolyte body 16 made of zirconia ceramics or the like, and further includes an outer measuring electrode (third electrode) 18 and an inner measuring electrode (fourth electrode) 20 which are disposed in alignment with each other on opposite surfaces of the solid electrolyte body 16. Thus, an electrochemical cell in the form of an oxygen concentration cell is formed. The outer and inner measuring electrodes 18, 20 are connected, through their leads, to a suitable external measuring device. In the aforementioned oxygen concentration sensing cell 4, an electromotive force due to difference in oxygen concentration is measured or detected between the outer measuring electrode 18 which is exposed to the outside measurement gas, and the inner measuring electrode 20 which is exposed to the atmosphere within the internal cavity 6.

The previously indicated cutout 22 for the internal cavity 6 is formed in the spacer member 8 in alignment with the inner pumping and measuring electrodes 14, 20 of the pumping and sensing cells 2, 4, and has substantially the same size as these electrodes 14, 20 in this specific example of FIG. 1.

This spacer member 8, and the oxygen pumping and sensing cells 2, 4 are laminated in stack with the spacer member 8 interposed between the two cells 2, 4, so that the openings of the rectangular cutout 22 in the spacer member 8 are closed by the upper and lower solid electrolyte bodies 10 and 16, more specifically, by the inner pumping and measuring electrodes 14 and 20 on the solid electrolyte bodies 10 and 16. Thus, the internal cavity 6 is defined by the electrodes 14, 20 which are exposed thereto, and the cutout 22 in the spacer member 8.

Figure 2:
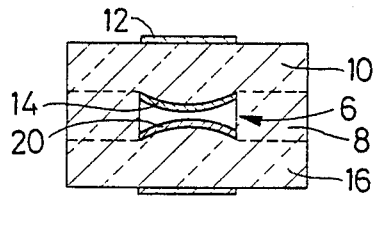
FIG. 2 is a schematic elevational view in cross section taken along line 2—2 of FIG. 1, showing the electrochemical device when produced according to the prior art process.

Incidentally, an electrochemical oxygen sensor of laminar structure as described hitherto is usually prepared by stacking unfired structures of the pumping and sensing cells 2, 4, and a ceramic green sheet of the spacer member 8, such that the green sheet of the spacer member 8 is sandwiched between the two unfired structures of the cells. The unfired structure of the pumping cell 2 consists of a green sheet (unfired layer) of the solid electrolyte body 10, and unfired layers of the pumping electrodes 12, 14 and their leads which are formed, as with a screen-printing method, on the opposite surfaces of the green sheet of the solid electrolyte body 10. Similarly, the unfired structure of the sensing cell 4 consists of a green sheet of the solid electrolyte body 16, and unfired layers of the measuring electrodes 18, 20 and their leads. These unfired elements are stacked under compressing pressure so as to form an unfired integral laminar structure, which is then co-fired at a suitable sintering temperature. In the process of preparing the unfired integral laminar structure, the portions of the green sheets of the solid electrolyte bodies 10, 16 located above and below the cavity 6 are displaced or extruded into the cavity 6 (due to the pressure exerted in the direction of thickness of the laminar structure to compress the layers of solid electrolyte bodies for better integration and bonding). As a result, the finally obtained electrochemical device has the internal cavity 6 whose volume and shape vary from those before the unfired laminar structure is compressed, as illustrated in FIG. 2. A variation in the volume of the cavity between the individual electrochemical devices will cause inconsistency in sensing characteristics from one device relative to another.

Figure 3:
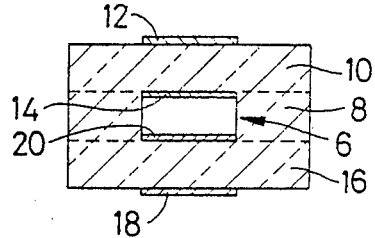
FIG. 3 is a schematic elevational view corresponding to FIG. 2, showing the electrochemical device when produced according to the process of the invention.

To avoid the above drawback, an insert in the form of a sheet made essentially of a material which sublimes at an elevated temperature is inserted, according to the invention, in the rectangular cutout 22 in the spacer member 8 while the unfired structures of the pumping and sensing cells 2, 4 and the green sheet of the spacer member 8 are stacked into the unfired laminar structure before this structure is compressed for better adhesion or bonding between the layers. In this unfired laminar structure, the insert filling the cavity 6 is positioned opposite to the unfired layers of the inner pumping and measuring electrodes 14 and 20, and thereby serves to prevent the adjacent portions of the green sheets of the solid electrolyte bodies 10, 16 from being displaced, deformed or extruded toward or into the otherwise existing space of the cavity 6. When the unfired integral laminar structure incorporating the sublimable insert in subsequently fired at an elevated temperature, the insert in the cavity 6 is sublimated and thus caused to disappear. Consequently, the the cavity 6 formed in the obtained electrochemcial device has substantially the same volume as designed or intended, as shown in FIG. 3. In other words, the use of the insert prevents the otherwise possible deformation of the unfired green sheets of the solid electrolyte bodies 10, 16, and thus makes it possible to provide the individual electrochemical devices with an internal cavity which has the same volume and configuration, i.e., volume and shape as intended.

The green sheets of the solid electrolyte bodies used in the present invention may be made of beta-alumina, aluminum nitride, NASICON, $SrCeO_3$, solid solution of bismuth oxide-oxide of rare earth element, $La_xCa_{1-x}YO_{3-a}$, as well as the previously indicated zirconia ceramics which are preferably used in the invention. Generally, the materials for the solid electrolyte bodies are used in the form of powder. For better formation into the intended planar shape, the powder is admixed with suitable binder and plasticizer, and/or other additives such as sintering aid and crystalline-phase stabilizer. The mixture is formed into the green sheets of the solid electrolyte bodies 10, 16 and spacer member 8 as illustrated in FIG. 1.

The binder (resin) to be included in the unfired solid electrolyte bodies (green sheets or layers)) may be polyvinly butyral, polymethyl methacrylate, ethyl cellulose, etc. Generally, such binders are used in an amount of about 5-10% by weight. The unfired solid electrolyte bodies may include, as a plasticizer, phthalic acid ester such as dioctyl or dibutyl phthalate, and/or polyethylene glycol, etc, in an amount of about 3-10% by weight. In the case where zirconia ceramics are used for the solid electrolyte bodies, alumina, silica, and/or clay are used as a sintering aid. Further, the zirconia ceramics may include, as a crystalline-phase stabilizer, $Y_2O_3$, $Yb_2O_3$, $Sc_2O_3$, $Nd_2O_3$, $Sm_2O_3$, $CaO$, $MgO$, and/or compounds such as nitrate, carbonate, etc., capable to produce such oxide(s) by heat. Such stabilizers are used in a molar amount of about 3-15% with respect to zirconia.

To prepare the unfired structures of the oxygen pumping cell 2 and the oxygen concentration sensing cell 4, unfired layers of the first, second, third and fourth electrodes (12, 14, 18, 20) and their leads are formed, as with a screen-printing method, on the appropriate surfaces of the green sheets of solid electrolyte of the composition which has been described. The unfired layers of these electrodes and their leads comprise, as their major components, at least one element of the platinum group including platinum, palladium, rhodium, iridium, ruthenium and osmium. The printed layers are finally fired into the electrodes and leads.

While the compositions of the green sheets of solid electrolyte and unfired layers of electrodes, and the methods of forming such green sheets and layers have been illustrated by way of example only, it will be obvious that the invention is not limited thereto, but other suitable technologies available in the art may be applied to fabricate the pumping and sensing cells.

It is noted that the insert to be disposed according to the invention in the internal cavity 6 in the unfired integral laminar structure of the solid electrolyte bodies (10, 16), should completely disappear or cease to exist in or after subsequent process of sintering of the unfired laminar structure at an elevated temperature. Stated differently, the insert must essentially be made of a sublimable material which can sublime by heat applied to fire the laminated assembly. In addition, the insert must have a volume sufficient to resist the extruding or expanding force of the green sheets against the insert while the green sheets are compressed for better integration and boding thereof in the process of preparation of the unfired laminar structure. Further, it is generally recommended that the sublimable material for the insert should not sublime at ordinary or room temperatures, and be highly insoluble in an organic solvent such as ether used as a solvent for preparing a paste for the insert. In particular, it is preferred to select the sublimable material which sublimes at a temperature higher than the decomposition point of the thermally decomposable binder, plasticizer and other substances contained in the green sheet of solid electrolyte. As the sublimable materials for the insert used according to the invention, theobromine, indigo, 1,5-diaminoanthraquinone, hexabromobenzene, naphthacene, etc. are particularly recommended.

Like the green sheets of solid electrolyte, the sublimable materials for the insert are admixed with suitable additives such as binder and plasticizer, and the mixture is formed into an unfired solid mass of intended shape and volume. Thus, the insert is prepared.

The insert which consists essentially of the above indicated sublimable material is formed preferably in substantially the same size and shape as the internal cavity 6, in view of its function of preventing the displacement or deformation of the adjacent portions of the green sheets of solid electrolyte. In other words, it is preferred to fill the cavity 6 with the insert, without a gap therebetween. However, it is not necessarily a requirement to fill the entire volume of the cavity 6 with the mass of the insert, provided the insert is sufficiently capable of preventing the deformation of the green sheets. It is thus possible to use a hollow insert or an insert of other suitable structures and configuration than described above.

The following example demonstrates steps of one preferred embodiment of the process of the invention to further manifest the technical features of the instant process.

EXAMPLE

Yttrium nitrate was added, as a stabilizer, to zirconia powder, so that the molar proportion of $Y_2O_3/ZrO_2$ was 4/96. The mixture was then mixed in a ball mill, and calcined at 900° C. for two hours. Subsequently, the calcined mass was ground into coarse particles by a roll crusher, and one part by weight of clay was added as a sintering aid to 99 parts by weight of the crushed mixture. Further, 0.5% by weight of ethylene glycol was added as a ground aid to the mixture. Then, the final mixture was dry grinding in a ball mill for 24 hours.

Successively, 100 parts by weight of the prepared zirconia powder with the additives was mixed, in a ball mill for 16 hours, with 8 parts by weight of polyvinyl butyral and 100 parts by weight of trichloroethylene, and a slurry of 600 poise was obtained. The slurry was then formed into a sheet of 0.8 mm thickness with a doctor-blade method, and the sheet was dried at 50° C.

for 12 hours. In this manner, an unfired zirconia sheet of 0.6 mm thickness was prepared.

In the next step, the unfired sheet of zirconia was cut into 5 mm×40 mm green sheets. With a paste of platinum, first and second unfired electrode layers were screen-printed as the outer and inner pumping electrodes 12, 14 on the opposite surfaces of one of the green sheets, whereby a first unfired structure (for the oxygen pumping cell 2) was prepared. Similarly, third and fourth unfired electrode layers were screen-printed as the outer and inner measuring electrodes 18, 20 on the opposite surfaces of another green sheet, whereby a third unfired structure (for the pumping cell 4) was obtained. The layers of the second and fourth electrodes 14, 20 were both formed in a rectangular layer of 3 mm×4 mm dimensions. Another green sheet was processed at a portion thereof to form the cutout 22 of 3 mm×4 mm dimensions as shown in FIG. 1. Thus, a second or central unfired structure was prepared.

As sublimable materials for the insert, 100 parts by weight of theobromine, 10 parts by weight of polyvinyl butyral, 200 parts by weight of trichloroethylene, and 6 parts by weight of dioctyl phthalate were introduced into a ball mill, and mixed for two hours to obtain a slurry. After the viscosity had been adjusted to 100 poise, the slurry was formed into a sheet of 0.8 mm thickness with a doctor-blade method. The sheet was left at 50° C. for 12 hours for drying, and a theobromine sheet of 0.6 mm thickness was obtained. The theobromine sheet was then cut into 3 mm×4 mm sheets.

The thus prepared 3 mm×4 mm theobromine sheet was inserted in the cutout 22 formed in the second unfired structure. The first, second and third unfired structures were superposed on each other so that the second unfired structure was sandwiched by the first and third unfired structures, and the assembly was heated and compressed into an unfired integral laminar structure, which was then fired at 1500° C. for two hours. Thus, the electrochemical device (oxygen sensor) was finally produced.

Ten pieces of such electrochemical devices were prepared according to the process of the invention as described above, and corresponding ten pieces of known electrochemical devices were prepared as comparative examples according to the traditional process wherein no insert was disposed in the internal cavity. These products of the invention and the prior art were tested for comparison of their operational results.

The electrochemical devices were placed in a exhaust gas at 600° C. produced by a propane gas burner at A/F ratio of 20. Power was applied to the oxygen pumping cell 2 so that a 2 mA current flows in a direction from the outer pumping electrode 12 toward the inner pumping electrode 14, in order to pump out the oxygen from the cavity 6. The direction of flow of the current through the pumping cell 2 was reversed when the electromotive force generated from the oxygen sensing cell 4 due to difference in oxygen concentration between the atmosphere in the cavity 6 and the outside combustion exhaust gas (measurement gas) reached 600 mV. With the reversal of the current flow, the oxygen in the exhaust gas was pumped into the cavity 6. This pumping-in operation was continued until the electromotive force of the oxygen sensing cell 4 reached 0 mV. At this moment, the direction of flow of the current through the pumping cell 2 was again reversed and held in this condition until the electromotive force generated from the oxygen sensing cell 4 reached 600 mV level.

The above cycle was repeated to measure the frequency or time interval at which the 600 mV level of electromotive force was cyclically obtained in the sensing cell 4. Variation in this time interval between the devices was observed.

The observation of the electrochemical devices produced according to the prior art process revealed that the average cycle was 320 msec ($\sigma=30\%$), while the average cycle of the devices obtained according to the instant process was found to be 540 msec ($\sigma=6\%$). Thus, the test showed that the electrochemical devices manufactured according to the invention were remarkably superior in operating stability to those of the prior art.

While the process of the invention has been illustrated in association with one preferred form of the electrochemical device, the principle of the invention may be applied to electrochemical devices of other type or construction. For example, the process of the invention is applicable to the manufacture of electrochemical devices as illustrated in FIGS. 4, 5, 6, 7-8 and 11-12.

Figure 4:
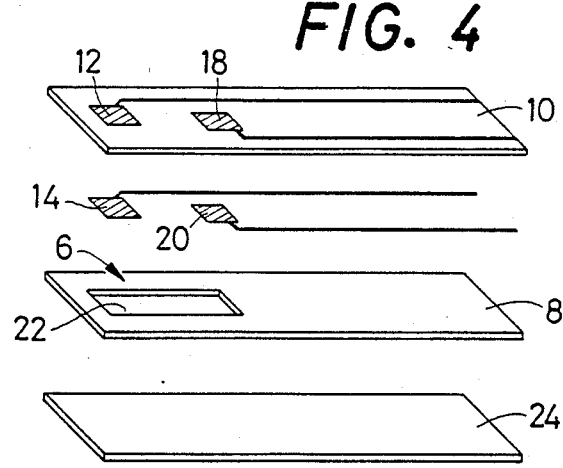
FIGS. 4, 5 and 6 are views corresponding to FIG. 1, illustrating other examples of the oxygen sensor as electrochemical devices to which the invention is applicable.

Stated more specifically, an electrochemical device of FIG. 4 is different from that of FIG. 1 in that the outer and inner measuring electrodes 18, 20 as well as the outer and inner pumping electrodes 12, 14 are disposed on the opposite surfaces of the first planar solid electrolyte body 10 of the pumping cell 2. The pumping electrodes 12, 14 are disposed in alignment with each other while the measuring electrodes 18, 20 are located in alignment with each. Further, the outer pumping and measuring electrodes 12, 18 are disposed on the outer surface of the solid electrolyte body 10, while the inner pumping and measuring electrodes 14, 20 are disposed on the inner surface of the solid electrolyte body 10. The inner pumping and measuring electrodes 14, 20 are both exposed to the cutout 22 (for the internal cavity 6) formed in the spacer member 8, as an elongate rectangular recess. The cutout 22 is covered at its bottom by a covering member 24 of solid electrolyte, whereby the cavity 6 is defined in the assembly, in the form of an elongate rectangular flat space along which the second and fourth electrodes 14, 20 are disposed in spaced-apart relation with each other on the inner surface of the solid electrolyte body 10.

As indicated above, the internal cavity 6 is defined by the spacer member 8 having the elongate rectangular cutout 22, and by the solid electrolyte body 10 and covering member 24 which sandwich the spacer member 8. In this case, too, an insert is used according to the principle of the invention so that it is disposed in the cutout 22 formed in the spacer member 8, that is, in the cavity 6 while the unfired integral laminar structure is prepared. With the use of this insert, the volume and shape of the cavity 6 will not vary when the green sheets of the members 10, 8 and 24 are stacked under compression pressure into the unfired laminar structure, which will be co-fired into the final product.

Figure 5:
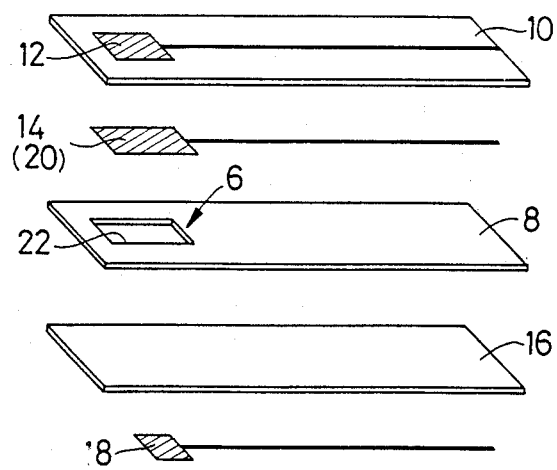

In the electrochemical device shown in FIG. 5, the inner pumping and measuring electrodes 14, 20, which are separate electrodes in FIG. 1, are provided in the form of a single layer of electrode. In this arrangement, it is necessary that the spacer member 8 be made of zirconia ceramics or other solid electrolyte.

Figure 6:
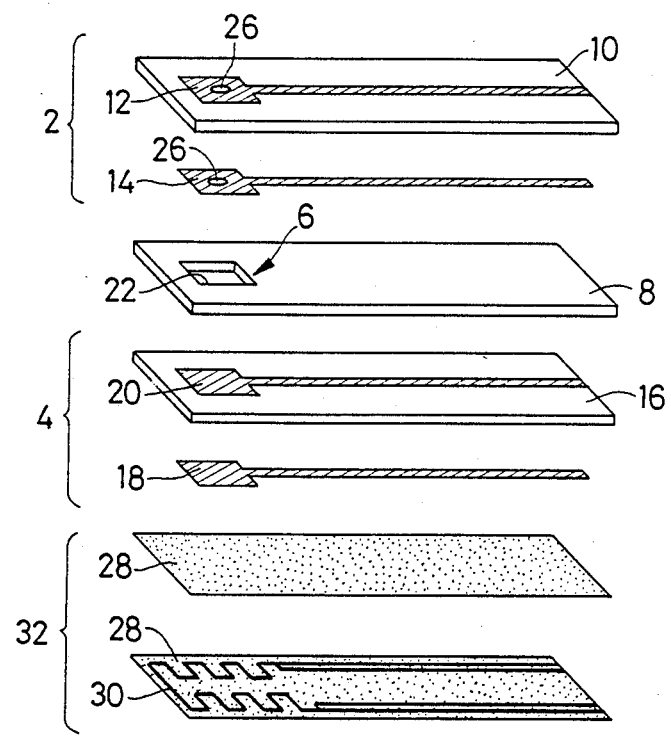

The electrochemical device of FIG. 6 is different from that of FIG. 1, in that the oxygen pumping cell 2 has a pin hole or aperture 26 formed through the thickness of a portion thereof at which the electrodes 12, 14 are disposed. In this arrangement, the measurement gas is introduced into the internal cavity 6 through the aperture 26, and the concentration of a component, i.e., oxygen in the cavity 6 is controlled through the pumping action of the pumping cell 2. The aperture 26 has a small diameter so that it provides a predetermined diffusion resistance to molecules of oxygen of the measurement gas. Another difference of this device from the device of FIG. 1 resides in the provision of a heater 32 disposed adjacent to the oxygen sensing cell 4. This heater 32 consists of a pair of porous electrically insulating layers 28, 28, and a heating element 30 sandwiched by the insulating layers 28, 28. This heater 32 is provided to heat the solid electrolyte bodies 10, 16 of the pumping and sensing cells 2, 4, with consideration given to the fact that the oxygen sensor is not capable of operating with sufficient reliability and accuracy while the temperature of the measurement gas is relatively low and the temperature of the solid electrolyte bodies 10, 16 are accordingly low.

Figure 7:
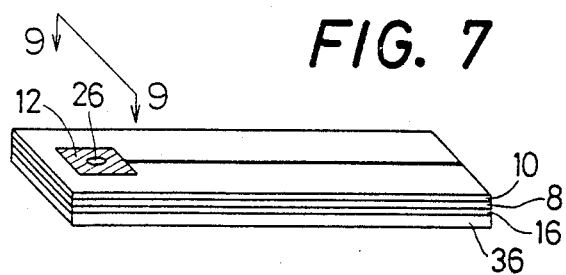
FIG. 7 is a perspective view of a further example of the oxygen sensor which can be manufactured according to the invention.
Figure 8:
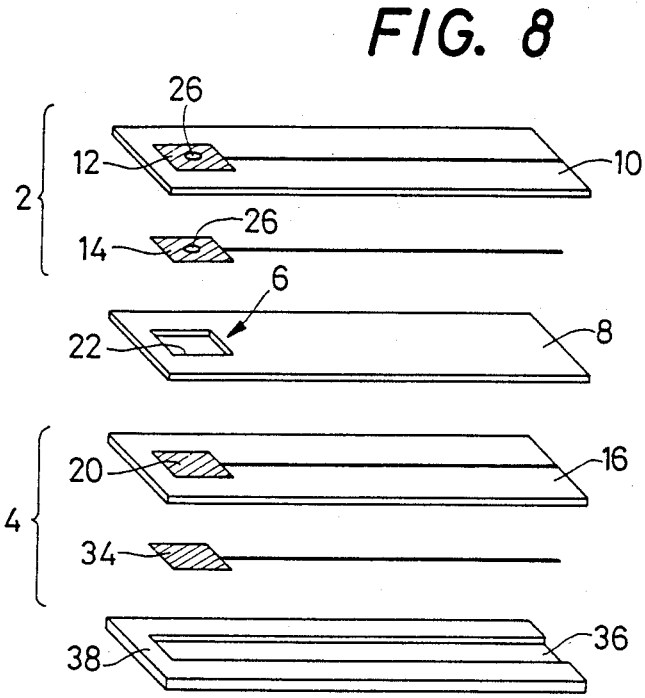
FIG. 8 is an exploded perspective view of the oxygen sensor of FIG. 7.

There is illustrated in FIGS. 7 and 8 a further modified form of the electrochemcial device whose oxygen concentration sensing cell 4 is different from those of the preceding arrangements. Described in more detail, the oxygen sensing cell 4 in the instant arrangement has the inner measuring electrode (fourth electrode) 20 on the inner surface of the solid electrolyte body 16 such that the electrode 20 is exposed to the cavity 6. However, the outer measuring electrode (third electrode) is disposed on the outer surface of the solid electrolyte body 16 so as to serve as a reference electrode 34 which is exposed to a reference gas such as the ambient air of a reference oxygen concentration that is introduced in a reference-gas passage 36 formed in a covering member 38 made of suitable solid electrolyte.

Figure 9:
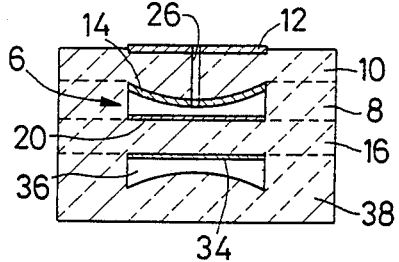
FIG. 9 is a schematic elevational view in cross section taken along line 9—9 of FIG. 7, illustrating the oxygen sensor when manufactured according to the prior art process.
Figure 10:
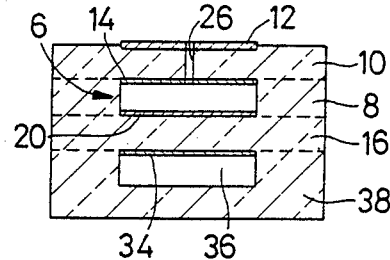
FIG. 10 is a schematic elevational view corresponding to FIG. 9, illustrating the oxygen sensor when manufactured according to the process of the invention.

The electrochemical device of the above construction has two spaces, i.e., cavity 6 and reference-gas passage 36 formed in the solid electrolyte bodies. Therefore, when the unfired laminar structure comprising the green sheets of solid electrolyte is prepared under compression pressure, the portions of the green sheets adjacent to the spaces 6, 36 are deformed, displaced or extruded into the spaces 6, 36, as shown in FIG. 9, whereby the volumes of these cavities are reduced. According to the invention, however, suitable inserts consisting essentially of sublimable materials are accommodated in these two spaces during the preparation of the unfired laminar structure before the latter is fired. As previously explained, the use of the inserts permits the obtained electrochemical device to be formed with the cavity 6 and reference-gas passage 36 having the same intended volume and shape, as depicted in FIG. 10.

While the electrochemical device shown in the above embodiments of FIGS. 7 and 8 has the pumping cell 2 and the cavity 6 as well as the sensing cell 4 and the reference-gas passage 36, it is to be understood that the process of the present invention is equally applicable to an electrochemical device which has neither a pumping cell nor an internal cavity as described hitherto. Stated differently, the instant process, wherein an insert of a sublimable material is used, may be practiced to manufacture an electrochemical device consisting of only an electrochemical sensing cell which has a reference-gas passage, a first electrode exposed to an outside measurement gas, and a second electrode exposed to the reference-gas passage.

Although the spacer member 8 used in all of the preceding examples of manufacture is made of solid electrolyte material, it may be made of alumina ceramics or other electrically insulating ceramics, provided the spacer member 8 is formed with the cutout 22 for defining the internal cavity 6.

Figure 11:
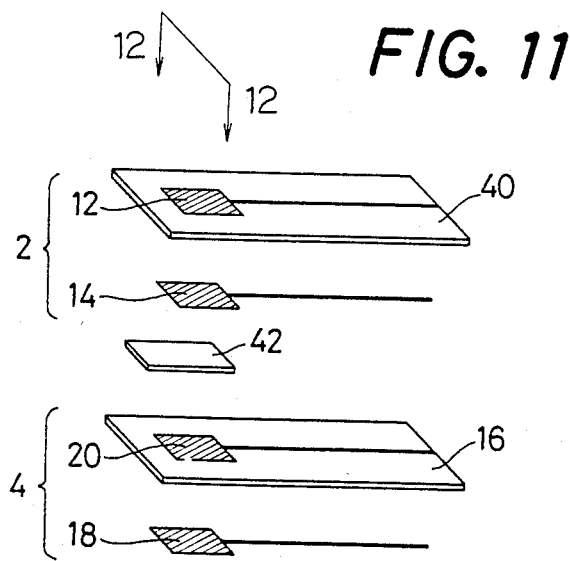
FIG. 11 is an exploded perspective view of a still further example of the oxygen sensor to which a modified form of the instant process is applicable.

The electrochemical device of FIG. 11 is an oxygen sensor wherein the spacer member 8 provided in the device of FIG. 1 is not used. Further, the device of FIG. 11 is different from the preceding devices in that the screen-printing process is employed throughout the preparation of the unfired laminar structure. More specifically, unfired layers of the outer and inner measuring electrodes 18, 20 are first screen-printed on opposite surfaces of a green sheet of the solid electrolyte body 16 to prepare an unfired structure for the oxygen sensing cell 4. Then, a paste consisting essentially of previously discussed thermally sublimable materials is applied by screen-printing on the unfired layer of the inner measuring electrode 20 to form an unfired layer 42 of the insert of suitable thickness, preferably 10–300 microns, for forming the cavity 6 of a suitable volume to which the inner pumping and measuring electrodes 14, 20 are exposed. Successively, layers of the inner pumping electrode 14, solid electrolyte body 40 and outer pumping electrode 12 are screen-printed on the layer of the insert and the green sheet of the solid electrolyte body 16. In this manner, the unfired integral laminar structure is prepared from the unfired structures of the pumping and sensing cells 2, 4 and the unfired insert layer 42. The desired electrochemical device is obtained by firing this unfired laminar structure at a suitable sintering temperature. Concerning the preparation of the unfired laminar structure of the electrochemical device, it is noted that the unfired layers of the oxygen pumping cell 2 are superposed on the unfired layer 42 of the insert and on the unfired layers of the oxygen sensing cell 4 such that the insert layer 42 is not entirely covered by the layers of the oxygen pumping cell 2, that is, partially exposed to the outside atmosphere at one of its longitudinal ends. Accordingly, the cavity 6, which is formed as a result of disappearance of the insert layer 42, is open to the atmosphere at its end, whereby the inner pumping and measuring electrodes 14, 20 are held in contact with the atmosphere introduced through the open end of the cavity 6. Since the thickness of the insert layer 42 is selected to fall with the above indicated range of 10–300 microns, the cavity 6 has a diffusion resistance to the molecules of oxygen in the outside measurement gas.

Figure 12:
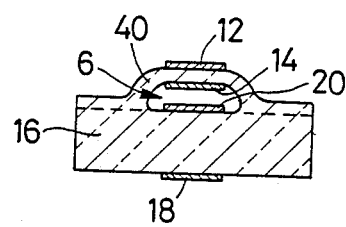
FIG. 12 is a schematic elevational view in cross section taken along line 12—12 of FIG. 11.

With the firing of the unfired laminar structure, the cavity 6 is formed as shown in FIG. 12, which maintains substantially the same volume and shape of the sublimable insert layer 42 due to the presence of the same during the process of preparation of the unfired laminar structure under pressure. This modified form of the process also permits the obtained electrochemical devices to operate with improved sensing stability.

While the process of the present invention has been described hitherto in connection with various types or configurations of electrochemical devices, it is to be understood that the invention is not confined to the precise forms of the illustrated examples of manufacture, but the principle of the invention may be practiced to manufacture other types of electrochemical devices without departing from the spirit and scope of the invention.

Although the process of the invention has been described as a method suitable for manufacturing the illustrated lean-burn sensors, the invention is also suitably applicable to lean-burn sensors of other types, and various other forms of oxygen sensors. Further, the invention is equally suitably used for producing various sensors and controllers for determining or controlling the concentration of specific components of a fluid associated with electrode reaction, such as nitrogen, carbon dioxide and hydrogen, other than oxygen.

What is claimed is:

1. A process of manufacturing an electrochemical device including an electrochemical pumping cell having a first and a second electrode, and an electrochemical sensing cell having a third and a fourth electrode, such that the electrodes are disposed on at least one of a plurality of planar solid electrolyte bodies and such that the second and fourth electrodes are exposed to an internal cavity formed in an assembly of the pumping and sensing cells, the process comprising the steps of superposing unfired layers of the solid electrolyte bodies, which contain at least a thermally decomposable binder, on each other to form an unfired integral laminar structure with unfired layers of the electrodes disposed on at least one of the unfired layers of the solid electrolyte bodies such that the internal cavity is formed with a desired volume in said unfired integral laminar structure and such that the unfired layers of the second and fourth electrodes are exposed to the internal cavity, wherein the improvement comprises the steps of:

interposing an insert having a volume less than or equal to said desired volume into said internal cavity to be formed during the superposition of said unfired layers of the solid electrolyte bodies and electrodes into said unfired integral laminar structure, such that said insert is disposed opposite to exposed surfaces of said unfired layers of the second and fourth electrodes to prevent deformation of said internal cavity, said insert comprising a sublimable material which sublimes at a temperature above a decomposition temperature of said binder; and co-firing said unfired integral laminar structure to sinter said laminar structure and result said sublimable material disappearing by means of sublimation.

2. The process of claim 1, wherein said insert has substantially the same size and shape as said internal cavity, and the cavity is substantially filled by said insert.

3. The process of claim 1, wherein said sublimable material is selected from the group consisting of theobromime, indigo, 1,5-diaminoanthraquinone, hexabromobenzene and naphthacene.

4. The process of claim 1, wherein said second and fourth electrodes are disposed on the same surface of the same solid electrolyte body.

5. The process of claim 4, wherein said internal cavity is an elongate rectangular flat space to which said second and fourth electrodes are exposed in a spaced-apart relation with each other along the surface of said same solid electrolyte body.

6. The process of claim 1, wherein said second electrode is disposed on one of said plurality of solid electrolyte bodies, and said fourth electrode is disposed on another of said plurality of solid electrolyte bodies.

7. The process of claim 6, wherein said insert is sandwiched between said unfired layers of the second and fourth electrodes.

8. The process of claim 1, wherein a single electrode serves commonly as said second and fourth electrodes.

9. The process of claim 1, wherein said first and third electrodes are disposed on the same surface of the same solid electrolyte body.

10. The process of claim 1, wherein a single electrode serves commonly as said first and third electrodes.

11. The process of claim 1, wherein a heater is disposed adjacent to said electrochemical pumping cell.

12. The process of claim 1, wherein a heater is disposed adjacent to said electrochemical sensing cell.

13. The process of claim 1, further comprising the step of forming diffusion-resistance means for communication between an outside measurement atmosphere and said internal cavity, said diffusion-resistance means having a predetermined diffusion resistance to molecules of a component of the outside measurement atmosphere.

14. The process of claim 13, wherein said diffusion-resistance means is formed by forming an aperture through thicknesses of said unfired layers of the first and second electrodes and through the solid electrolyte body of said electrochemical pumping cell in its green state, said aperture having a diameter selected so as to provide said predetermined diffusion resistance.

15. The process of claim 13, wherein said diffusion-resistance means is formed by opposing two electrochemical cells toward each other, said two electrochemical cells comprising an electrochemical pumping cell and an electrochemical sensing cell, with a gap therebetween said gap being selected so as to provide said predetermined diffusion resistance.

16. The process of claim 1, further comprising the steps of forming a reference-gas passage in said unfired integral laminar structure such that the unfired layer of the third electrode is exposed to said reference-gas passage, and interposing another insert consisting essentially of said sublimable material in said reference-gas passage before said unfired integral laminar structure is co-fired.

17. The process of claim 1, wherein said unfired layers of solid electrolyte further contain a plasticizer, and said sublimable material sublimes at a temperature above a decomposition temperature of said plasticizer.

18. A process of manufacturing an electrochemical device including an electrochemical pumping cell having a first and a second electrode, and an electrochemical sensing cell having a third and a fourth electrode, such that the electrodes are disposed on at least one of a plurality of planar solid electrolyte bodies and such that the third electrode is exposed to a reference gas existing in a reference-gas passage formed in an assembly of the electrochemical pumping and sensing cells, the process comprising the steps of superposing unfired layers of the solid electrolyte bodies, which contain at least a thermally decomposable binder, on each other to form an unfired integral laminar structure with unfired layers of the electrodes disposed on at least one of the unfired layers of the solid electrolyte bodies such that the reference-gas passage is formed with a desired volume in said unfired integral laminar structure and such that the unfired layers of the third electrode is exposed to the reference-gas passage, wherein the improvement comprises the steps of:

interposing an insert having a volume less than or equal to said desired volume into said reference-gas passage to be formed during the superposition of said unfired layers of the solid electrolyte bodies and electrodes into said unfired integral laminar structure, such that said insert is disposed opposite to an exposed surface of said unfired layer of the third electrode to prevent deformation of said reference-gas passage, said insert comprising a sublimable material which sublimes at a temperature above a decomposition temperature of said binder; and co-firing said unfired integral laminar structure to sinter said laminar structure and result said sublimable material disappearing by means of sublimation.

19. The process of claim 18, wherein said sublimable material is selected from the group consisting of theobromine, indigo, 1,5-diaminoanthraquinone, hexabromobenzene and naphthacene.

20. The process of claim 18, wherein said unfired layers of solid electrolyte further contain a plasticizer, and said sublimable material sublimes at a temperature above a decomposition temperature of said plasticizer.

21. A process of manufacturing an electrochemical device including an electrochemical sensing cell having a first and a second electrode, such that the electrodes are disposed on at least one planar solid electrolyte body, such that the first electrode is exposed to an outside measurement gas while the second electrode is exposed to a reference gas existing in a reference-gas passage formed in the device, the process comprising the steps of superposing unfired layers of said at least one solid electrolyte body, which contain at least a thermally decomposable binder, and said first and second electrodes into an unfired integral laminar structure such that the reference-gas passage is formed with a desired volume in said unfired integral laminar structure and such that the unfired layer of the second electrode is exposed to the reference-gas passage, wherein the improvement comprises the steps of:

interposing an insert having a volume less than or equal to said desired volume into the reference-gas passage to be formed during the superposition of said unfired layers of said at least one solid electrolyte body and said electrodes into said unfired integral laminar structure, such that said insert is disposed opposite to an exposed surface of said unfired layer of the second electrode to prevent deformation of said reference-gas passage, said insert comprising a sublimable material which sublimes at a temperature above a decomposition temperature of said binder; and co-firing said unfired integral laminar structure to sinter said laminar structure and result in said sublimable material disappearing by means of sublimation.

22. The process of claim 21, wherein said sublimable material is selected from the group consisting of theobromine, indigo, 1,5-diaminoanthraquinone, hexabromobenzene and naphthacene.

23. The process of claim 21, wherein said unfired layers of solid electrolyte further contain a plasticizer, and said sublimable material sublimes at a temperature above a decomposition temperature of said plasticizer.

* * * * *